United States Patent [19]

Foster

[11] Patent Number: 5,353,929
[45] Date of Patent: Oct. 11, 1994

[54] PACKAGE FOR SURGICAL INSTRUMENT

[75] Inventor: Brian W. Foster, Trumbull, Conn.

[73] Assignee: United States Surgical Corporation, Norwalk, Conn.

[21] Appl. No.: 49,483

[22] Filed: Apr. 19, 1993

[51] Int. Cl.⁵ .................................. B65D 83/10
[52] U.S. Cl. ................... 206/364; 206/438; 206/564; 206/471
[58] Field of Search .............. 206/363, 364, 365, 438, 206/564, 372, 373, 461, 471

[56] References Cited

U.S. PATENT DOCUMENTS

| | | | |
|---|---|---|---|
| 2,720,969 | 10/1955 | Kendall | 206/365 |
| 3,851,649 | 12/1974 | Villari | 206/564 |
| 3,910,410 | 10/1975 | Shaw | 206/363 |
| 4,324,331 | 4/1982 | Ignasiak | 206/363 |
| 4,366,901 | 1/1983 | Short | 206/364 |
| 4,645,079 | 2/1987 | Hill | 206/564 |
| 4,779,727 | 10/1988 | Taterka et al. | 206/364 |
| 5,031,775 | 7/1991 | Kane | 206/364 |
| 5,082,112 | 1/1992 | Dunklee | 206/363 |
| 5,144,942 | 9/1992 | Decarie et al. | 128/4 |
| 5,156,267 | 10/1992 | Yates, Jr. et al. | 206/364 |
| 5,165,540 | 11/1992 | Forney | 206/364 |
| 5,199,567 | 4/1993 | Discko, Jr. | 206/564 |

Primary Examiner—David T. Fidei

[57] ABSTRACT

A package for an elongated surgical instrument having a handle portion, an elongated body portion and a working distal end. The package includes a first channel for receiving the handle portion, a second channel for receiving the body portion and a third channel for receiving the working distal end. At least one flange retains the handle portion in the first channel and a second plurality of flanges retain the elongated body portion in the second channel.

12 Claims, 7 Drawing Sheets

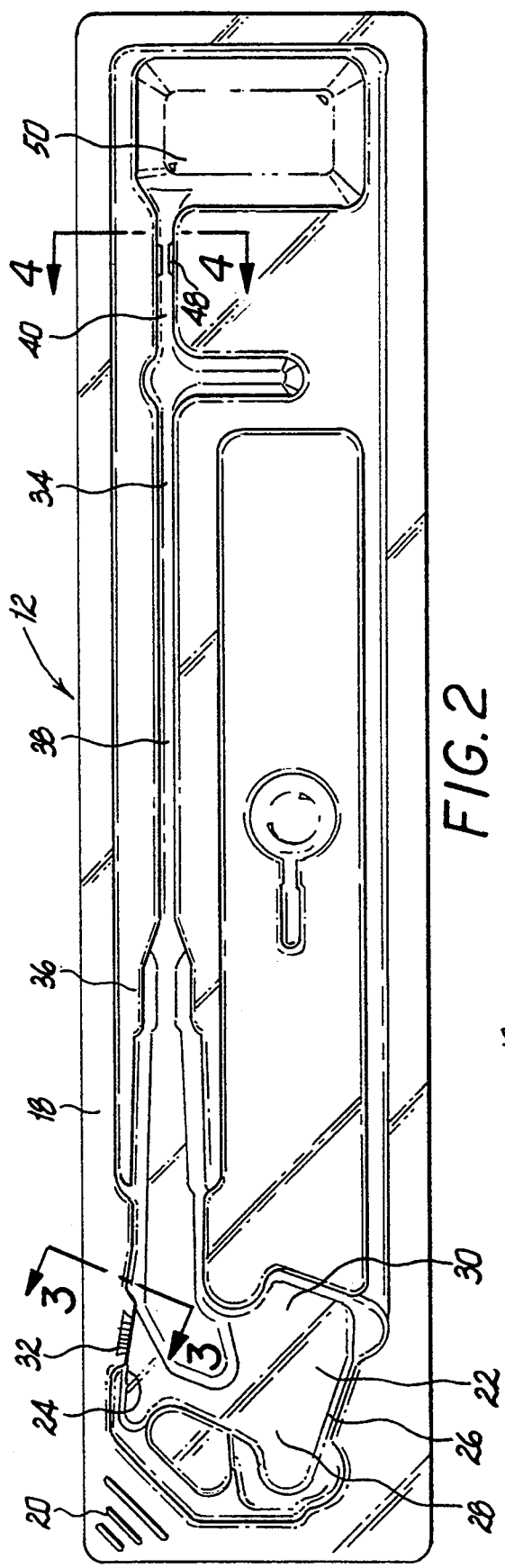
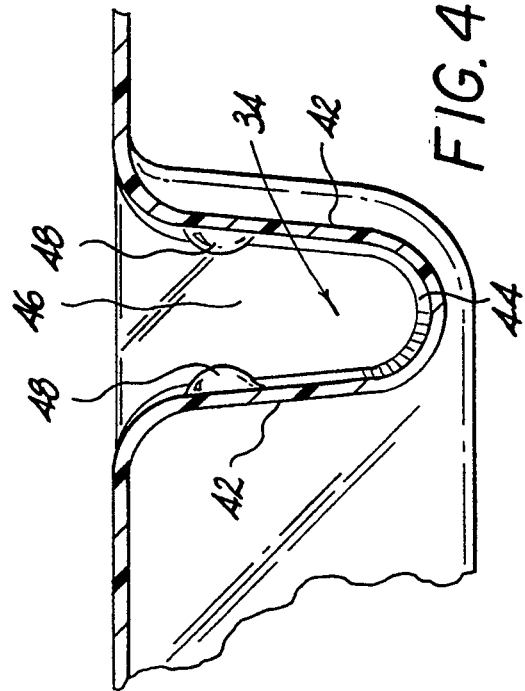
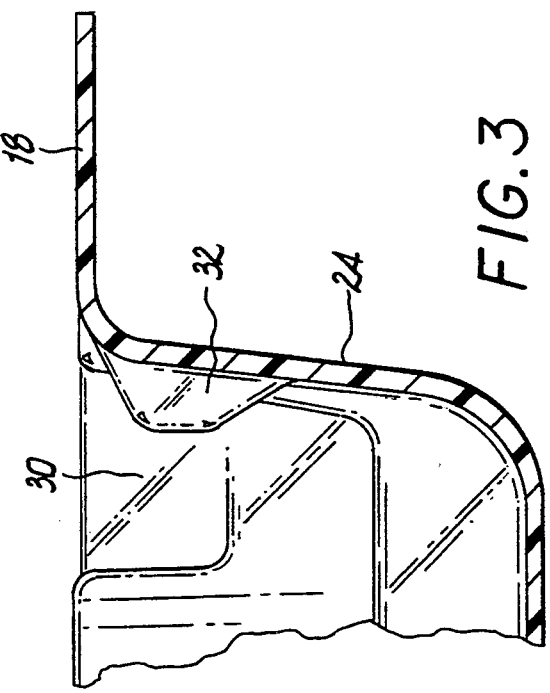

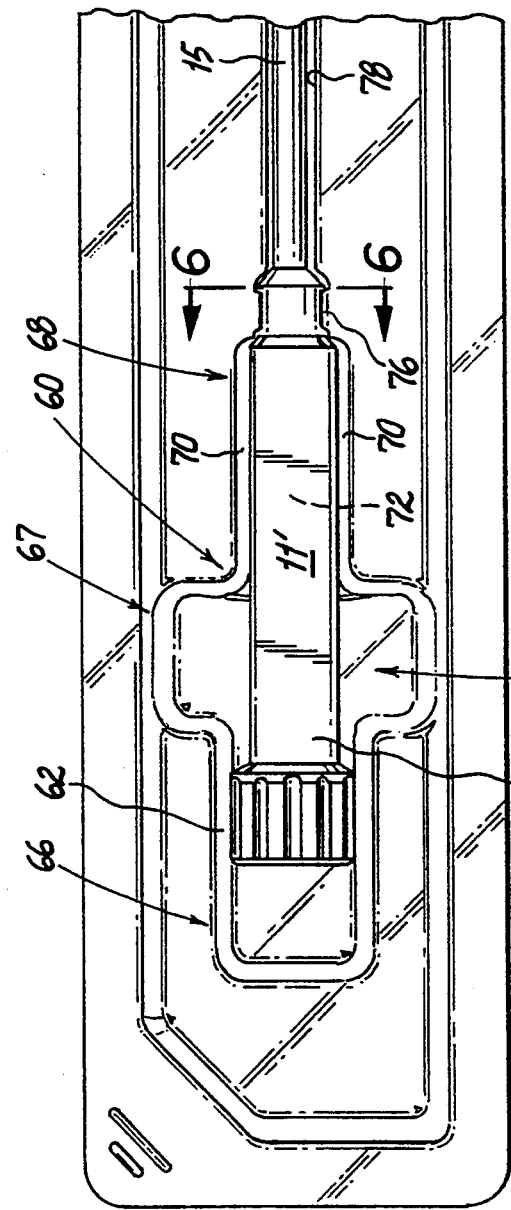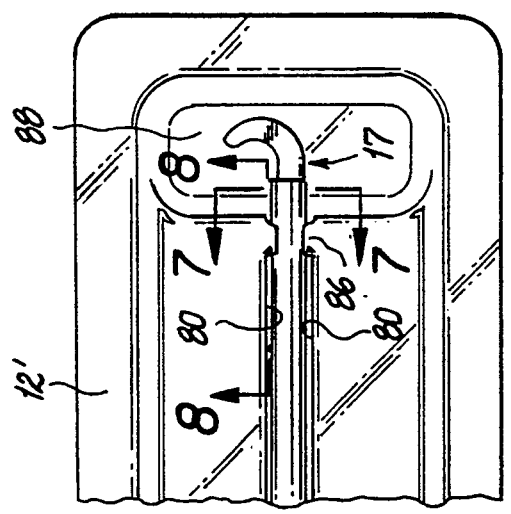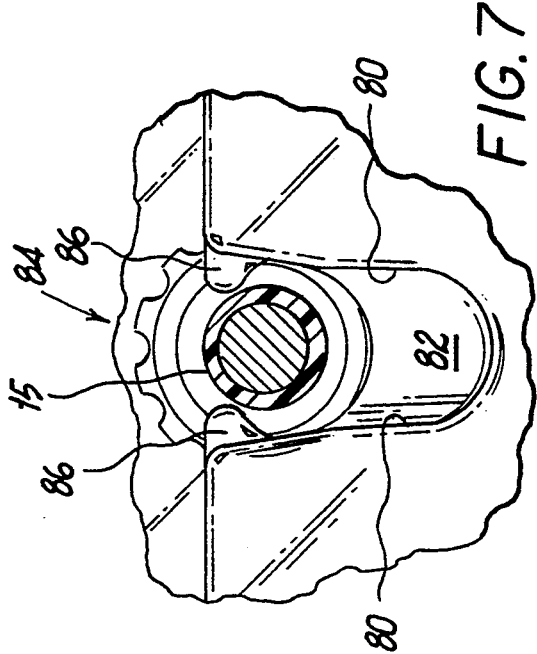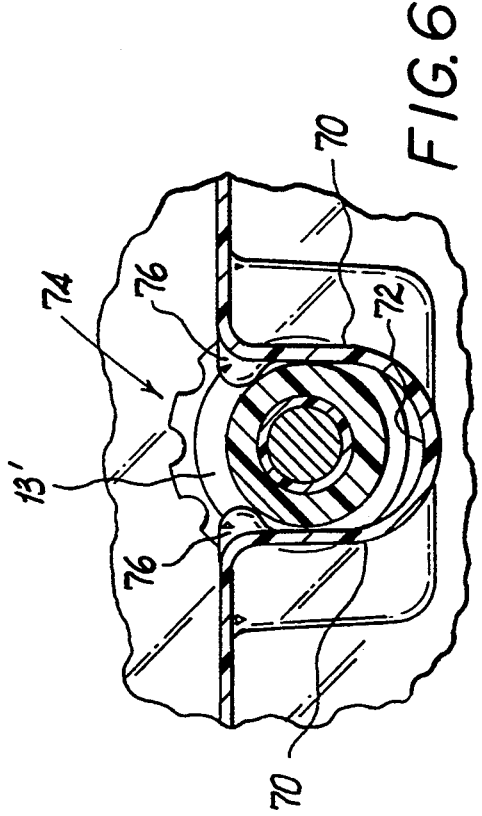

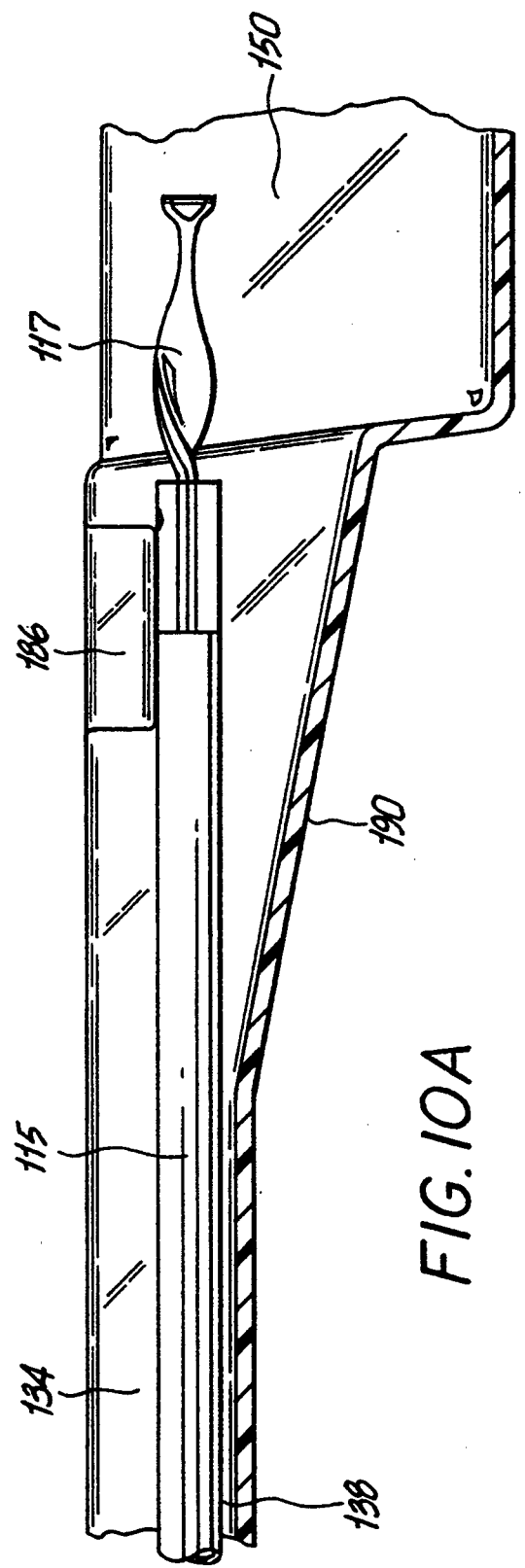
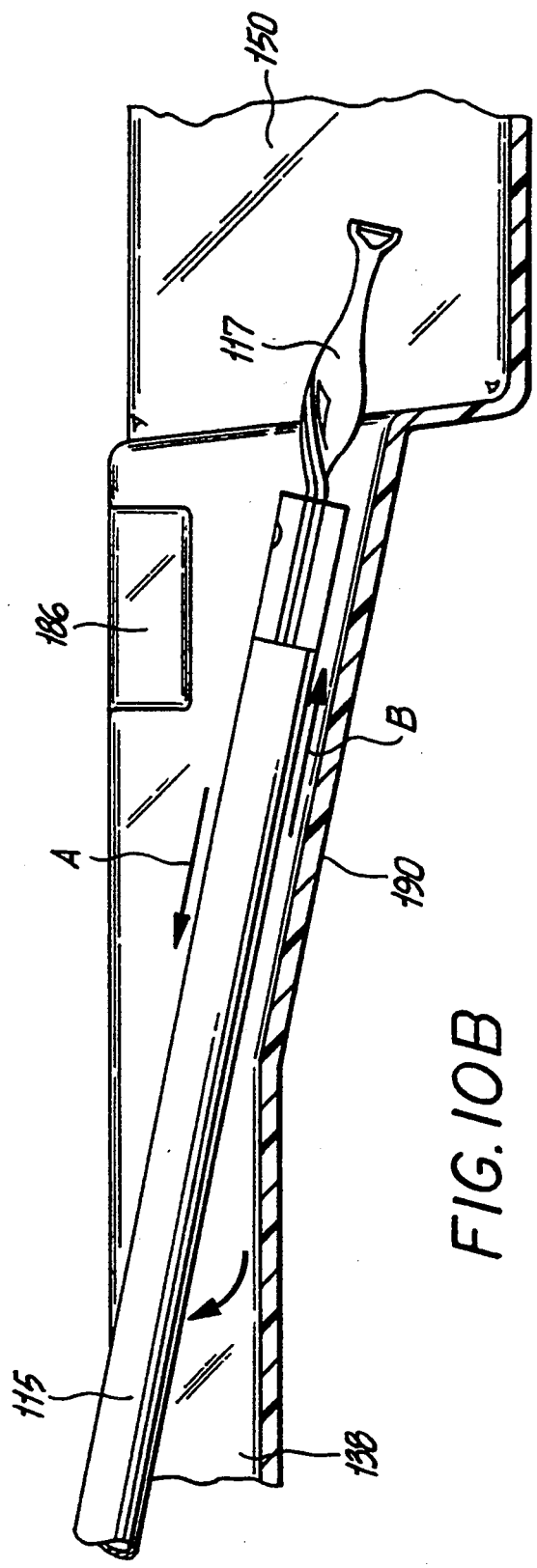

PACKAGE FOR SURGICAL INSTRUMENT

BACKGROUND OF THE INVENTION

1. Field of the Invention

The present invention relates to an instrument package for securely packaging an elongated surgical instrument which may also allow the instrument to be relatively easily withdrawn from the instrument package by a user.

2. Background of the Art

Various types of instrument packages are known for packaging elongated or endoscopic surgical instruments. One example of a package for an elongated or endoscopic surgical instrument is shown in U.S. Pat. No. 5,082,112 which discloses a packaging unit for an endoscopic ligating loop instrument, the packaging unit including a molded instrument holding member and a cover member. Another example of a package for an elongated surgical instrument is shown in U.S. Pat. No. 4,324,331 which discloses a bottom assembly containing at least one cavity for receiving an elongated surgical implement and a lid portion to cover the cavity. This package also includes a plurality of spaced apart cavities for selectively plating protective plugs at each end of the implement such that one packaging cavity may be used for various length instruments. Yet another example of a package for an elongated medical instrument is shown in U.S. Pat. No. 3,910,410 which discloses a tray having at least one cavity for receiving articles and a flange area upon which rests a lid for closing the at least one cavity. This package is resealable and includes two coatings of materials for resealing the lid to the tray.

The construction of a package for an elongated surgical instrument requires that the elongated instrument be securely held to prevent damage to the instrument itself and the sterilized package during shipping and storage. The package should also advantageously be constructed to facilitate placement into the package, and also be relatively easily releasable from the package by the user. The present invention is directed to a package for an elongated surgical instrument which provides the above properties.

SUMMARY OF THE INVENTION

Provided herein is a package for releasably holding an elongated surgical instrument having a handle portion, an elongated portion, and a working end member. The package includes a relatively rigid instrument holding member having a base. A cover member is mounted to and encloses the instrument holding member. A first channel for receiving the handle portion is formed in the base of the instrument holding member and conforms to the general shape of the handle portion. The instrument handle portion is retained in the first channel by at least one handle flange which extends from a side wall of the first channel. The handle flange is rigid enough to retain the handle portion and provides a camming surface about which the handle is pivoted to remove the handle from the first channel.

The package also includes a second channel formed in the base of the instrument holding member for receiving the elongated portion of the instrument. The second channel conforms to the general shape of the elongated portion received therein and is in communication with the first channel. In the preferred embodiment, a pair of oppositely positioned retainer flanges extend from the side walls of the second channel to frictionally engage or retain the elongated portion in the second channel. The retainer flanges are rigid enough to retain the elongated portion and yet flexible enough to deflect when the instrument is inserted into and removed from the second channel. The package also includes a third channel for receiving the working end of the surgical instrument.

In another embodiment of the invention, the handle portion of the instrument is received within a first channel which includes a pair of oppositely positioned flanges for retaining the handle therein. The elongated body of the instrument portion is received within a second channel and retained therein by a second pair of oppositely positioned body flanges. The body second channel includes a downwardly extending portion for angling the body portion to remove it from engagement with the second pair of flanges.

Yet another embodiment of the invention includes a first channel for receiving the handle portion of the instrument and having at least one handle flange extending from a side wall of the first channel for retaining the handle portion therein. A downwardly extending portion is formed in a second channel which receives the elongated body of the instrument. A pair of body flanges extend from the second channel and retain the instrument elongated body therein. The handle flange provides a surface for camming the handle portion and angling out from engagement by the handle flange. The downwardly extending portion permits the distal end of the elongated body portion to be angled and removed from engagement with the second pair of flanges.

BRIEF DESCRIPTION OF THE DRAWING

The accompanying drawings constitute part of the disclosure of the invention and illustrate preferred embodiments of the invention. The drawings may be briefly described as follows:

FIG. 2 is a plan view of the instrument holding member shown in FIG. 1;

FIG. 3 is a partial cross-sectional view of the instrument holding member of the package taken along line 3—3 of FIG. 2;

FIG. 4 is a partial cross-sectional view of the instrument holding member of the package taken along line 4—4 of FIG. 2;

FIG. 5 is a plan view of an instrument holding member in accordance with an alternative embodiment of the present invention;

FIG. 6 is a partial cross-sectional view of the instrument holding member of the package taken along the line 6—6 of FIG. 5;

FIG. 7 is a partial cross-sectional view of the instrument holding member of the package taken along line 7—7 of FIG. 5;

FIG. 10A is a partial cross-sectional view of one instrument holding member of the package taken along line 10—10 of FIG. 9 and shown in combination with a surgical instrument therein; and FIG. 10B is a partial cross-sectional view of one instrument holding member of the package taken along line 10—10 of FIG. 9 and shown in combination with a surgical instrument shown rotated therein and in the process of being removed therefrom.

DETAILED DESCRIPTION OF THE PREFERRED EMBODIMENTS

The package of the present invention provides means for packaging an elongated surgical instrument in a manner which prevents damage to the sterilized instrument and package during transportation and storage, yet also permits the instrument to be conveniently and easily removed by the user when desired. One type of surgical instrument for which this package is designed is an instrument having an elongated and relatively narrow member so that it may be inserted through a trocar cannula for use in minimally invasive surgical procedures, such as endoscopic procedures.

Figure 1:
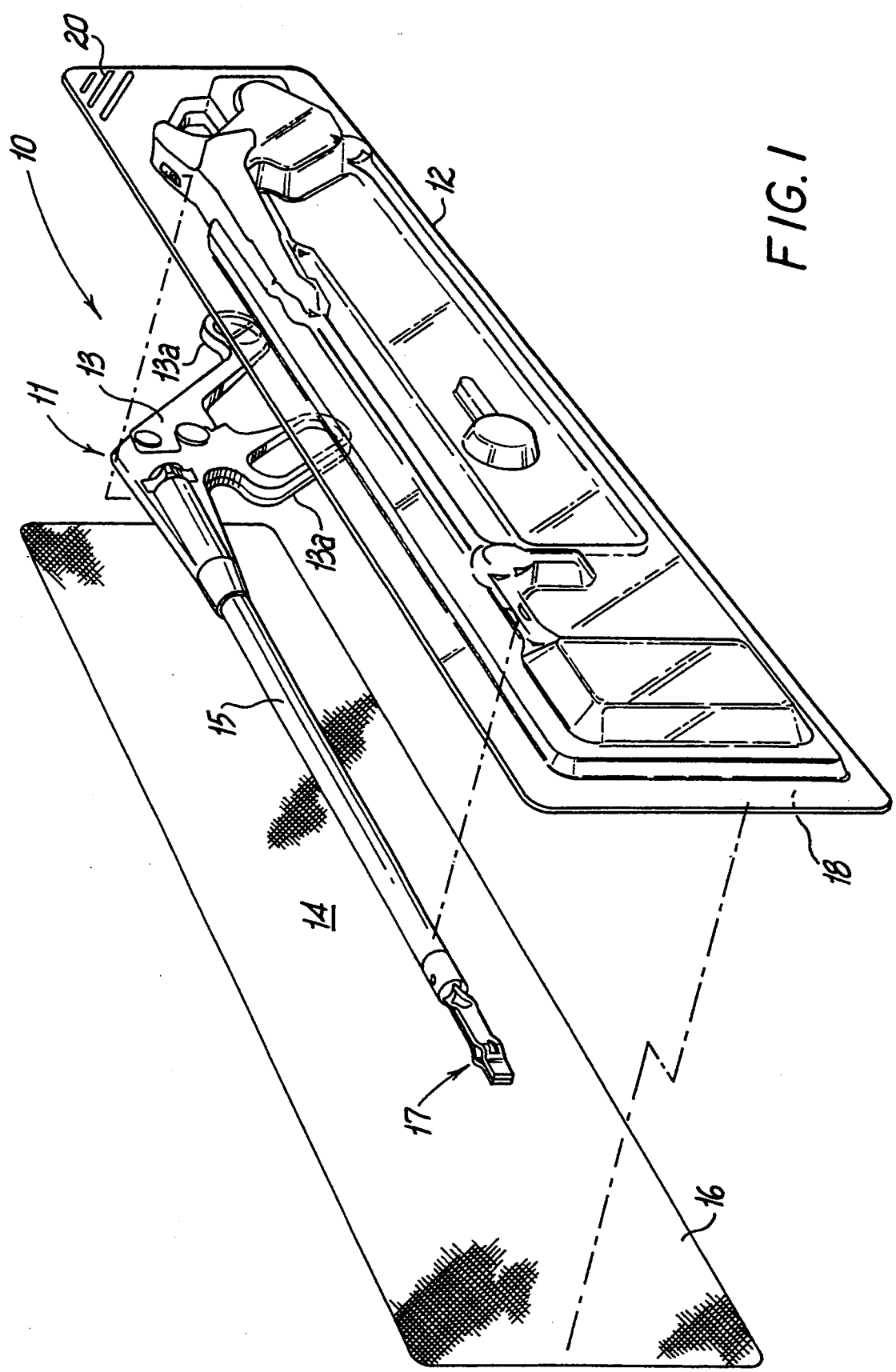
FIG. 1 is an exploded perspective view of a package in accordance with the invention shown in combination with an instrument holding member and a surgical instrument.

Referring to the first embodiment of the invention shown in FIGS. 1 and 2, an elongated surgical instrument package 10 for holding an elongated surgical instrument 11 is shown. The elongated instrument includes a handle portion 13, an elongated portion 15, and a working end 17. One such type of elongated surgical instrument is the ENDO BABCOCK ® (United States Surgical Corporation) 10 mm instrument sold by United States Surgical Corporation.

The package 10 includes a relatively rigid molded instrument holding member 12 and a peelable or strippable cover member 14 which is capable of maintaining the sterile condition of the package contents. Instrument holding member 12 and cover member 14 can be fabricated from any suitable materials. Advantageously, instrument holding member 12 is molded from a resin and preferably a transparent recycleable resin, such as polyethylene terephthalate. Cover member 14 is advantageously formed from a spunbonded material, e.g., of high density polyethylene fiber, such as TYVEK ® (DuPont) which is ideal for ethylene oxide sterilization. Numerous other materials, both polymeric, non-polymeric and combinations thereof, e.g., aluminum foil-polymer laminates, can be utilized for the construction of instrument holding member 12 and/or cover member 14 as will be readily appreciated by those skilled in the art. In the sealed condition of the package, cover member 14 is bonded along its perimeter region 16 to perimeter region 18 of instrument holding member 12 employing any suitable adhesive. The perimeter region 18 of the instrument holding member 12 is formed in a first and uppermost plane of the rigid instrument holding member 12. A knurled section 20 at the proximal end of instrument holding member 12 is not bonded to cover 14 and facilitates gripping of the cover 14. Access to the package is provided by gripping the cover 14 in one hand and holding the knurled section 20 in the other and pulling back of the cover member 14.

The rigid instrument holding member 12 includes a first channel 22 which extends for at least the full length and width of the handle 13 and prevents the handle 13 from shifting about in the package, preferably through frictional engagement with the handle. The first channel 22 includes an upper portion side wall 24, a lower portion side wall 26, a bottom wall 28 and an open top 30. A handle retaining flange 32 extends from the upper portion 24 of the first channel 22 and extends over a portion of open top 30 to retain the handle 13 within the handle channel 22. As best seen in FIG. 3, the handle retaining flange 32 extends from the side wall 24 of the first channel 22. The retaining flange 32 is preferably integral with the side wall 24, and rigid enough to retain the handle portion 13 in the first channel 22. The retaining flange 32 further acts as a camming surface about which the handle 13 is pivoted in order to remove the instrument 11 from the instrument holding member 12.

A second channel 34 is formed in the rigid instrument holding member 12 and extends for at least the full length of the elongated tubular body 15 and prevents the body 15 from shifting about in the package, preferably through frictional engagement with the elongated tubular body. The second channel 34 includes a proximal portion 36, a middle portion 38 and a distal portion 40. The second channel 34 is formed by a pair of oppositely positioned side walls 42, a bottom wall 44 and an open top 46. The second channel 34 is formed in a second plane which is below the first plane of the holding member perimeter 18.

The elongated tubular body 15 is retained within the second channel 34 by a second pair of flanges. 48 which extend over a portion of the second channel 34. As best seen in FIG. 4, the second pair of flanges 48 extend oppositely from the middle portion side walls 42 of the second channel 34 to hold the distal portion of the elongated tubular body 15. The flanges 48 are preferably integral with the side walls 42, and are rigid enough to retain the tubular body 15 in the second channel 34, yet are also flexible enough to deflect when the elongated body 15 is inserted into or removed from the second channel 34 by being frictionally forced past flanges 48. A third channel 50 is formed in the rigid instrument holding member 12 and receives the distal working end 17 of the instrument. The third channel 50 is also used as a balancing foot for the packages when they are placed individually or stacked upon each other.

Figure 3B:
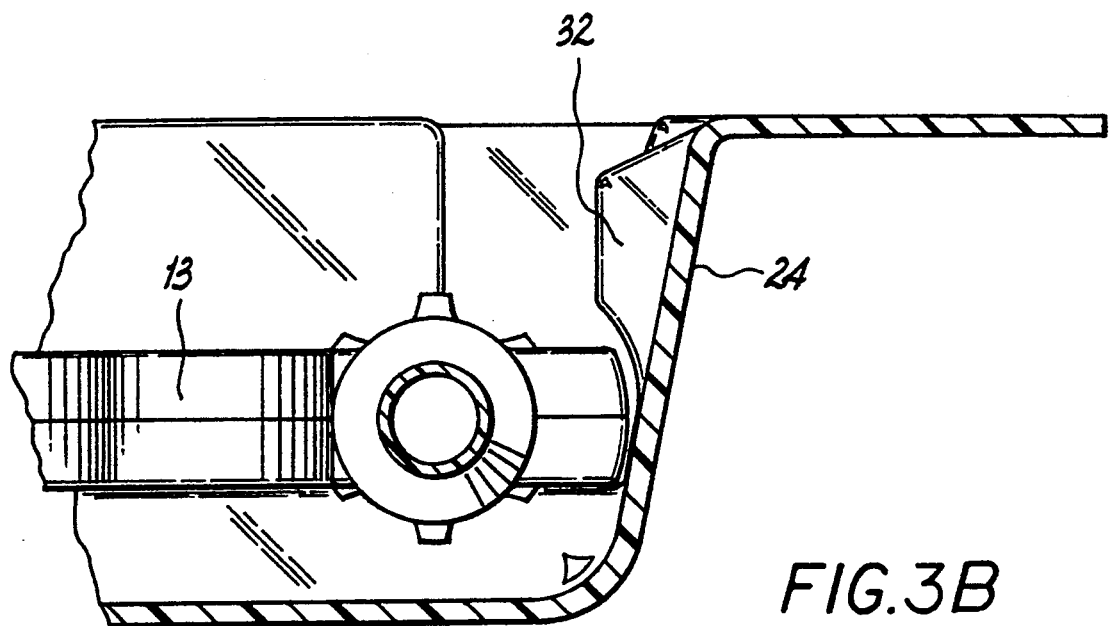
FIG. 3B is a partial cross-section view of the instrument holding member of the package taken along line 3—3 of FIG. 2 and shown in combination with a surgical instrument retained therein.
Figure 3A:
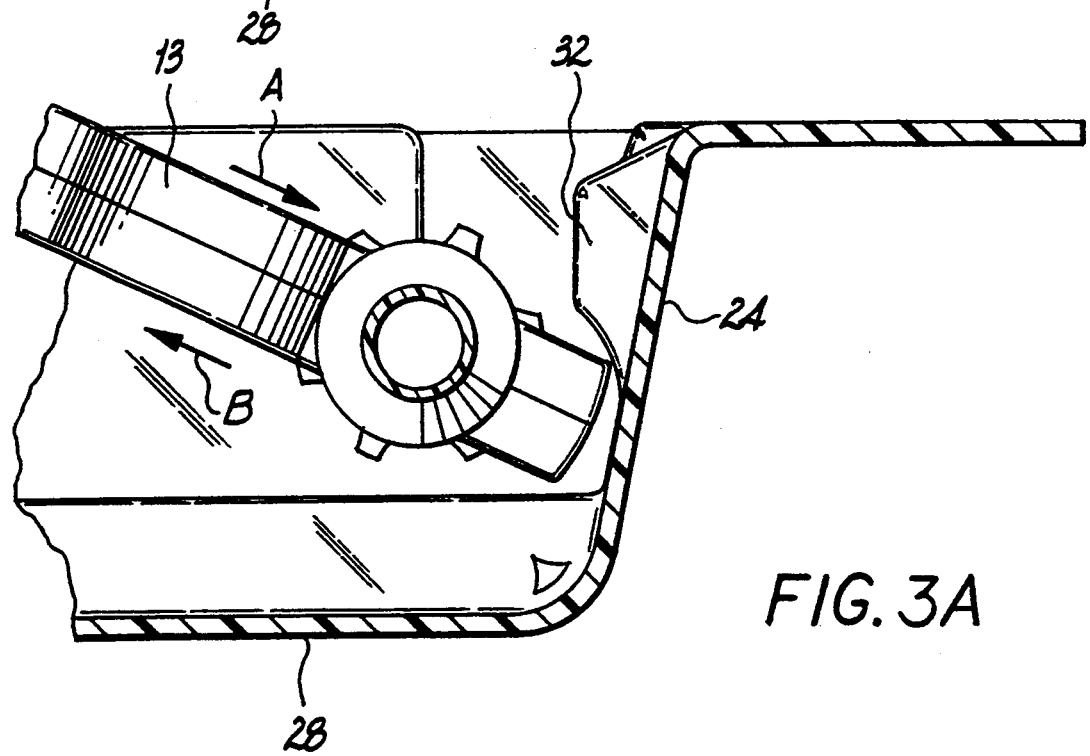
FIG. 3A is a partial cross-section view of the instrument holding member of the package taken along line 3—3 of FIG. 2 and shown in combination with a surgical instrument rotated therein.

In use, the surgical instrument 11 is loaded into the rigid instrument holding member 12 by angling and inserting the distal working end 17 of the instrument under the second pair of flanges 48. Preferably during insertion, the finger ring portions 13a of the handle 13 extend perpendicularly away from the rigid instrument holding member 12 and in the direction of open top 30. As shown in FIG. 3A, the upper portion of the handle 13 is angled and inserted towards the upper portion side wall 24 and in the direction indicated by arrow A under the handle retaining flange 32. The upper portion of the handle 13 is then engaged by the handle retaining flange 32 as is shown in FIG. 3B. The finger ring portions 13a of the handle are then rotated and released, such that the instrument handle 13 is retained within the first channel 22.

The surgical instrument 11 is released from the instrument holding member 12 by first grasping the finger ring portions 13a of the handle 13 and rotating the finger ring portions 13a away from the instrument holding member 12 and towards open top 30. This rotation of the finger ring portion 13a causes the upper portion of the handle 13 to be rotated as shown in FIG. 3A. As the upper portion of the handle 13 is pivoted about the handle retaining flange 32, the handle portion 13 is cammed about and removed from its engagement with the handle retaining flange 32, and further removed from the first channel 22. While grasping the handle portion 13, the working distal end 17 of the instrument is released from its engagement by the pair of flanges 48 by pulling, in a proximal direction, the distal end of the elongated body 15 under the second pair of flanges.

Referring to the second embodiment of the invention shown in FIG. 5, the instrument holding member 12' has many similar features shown in FIG. 1 but in this embodiment the package retains an elongated surgical instrument 11' having an elongated handle 13', such as an ENDO RETRACT MAXI ® (United States Surgical Corporation). In this embodiment, a first portion 60 is formed in the instrument holding member 12' and extends for at least the full length of the handle portion 13' and prevents the handle 13' from shifting about in the package, preferably through frictional engagement with the handle 13'. The first portion 60 includes a proximal portion 66, a middle portion 67 and a distal portion 68. The middle portion 67 of the portion 60 includes a grasping portion 64 for facilitating removal of the instrument 11' from the instrument holding member 12'. The first portion 60 further includes a pair of oppositely positioned side walls 70, a bottom wall 72 and an open top 74. The instrument handle portion 13' is retained within the first portion 60 by a first pair of retaining flanges 76 which extend partially over the first portion 60 to hold the middle portion of the handle portion 13'. As best seen in FIG. 6, the first pair of flanges 76 extend oppositely from the side walls 70 of the first portion 60. The flanges 76 are preferably integral with the side walls 70, and are rigid enough to retain the handle portion 13' in the first portion 60, but sufficiently flexible to deflect when the handle portion 13' is inserted into or removed from the first portion 60 by being frictionally forced past the first flanges 76.

A second channel 78 communicates with the first portion 60, is formed in the same plane as the first portion 60 and conforms to the general shape of the elongated body 15 which is retained therein, The second channel 76 is formed by a pair of side walls 80, a bottom wall 82 and an open top 84. The elongated body portion 15 is frictionally retained in the second channel 78 by a pair of oppositely positioned body flanges 86. As best seen in FIG. 7, the body flanges 86 extend from the side walls 80 of the second channel 78 and are integral therewith. The body flanges 86 are rigid enough to retain the elongated body portion 15 of the instrument within the second channel 78, but flexible to deflect somewhat when the elongated body portion 15 is inserted into or removed from the second channel 78 by being frictionally forced past the body flanges 86. As shown in FIG. 5, the distance between each flange of the first pair of flanges 76 is greater than the distance between each flange of the pair of body flanges 86. The reduced distance between the pair of body flanges 86 further enhances the retaining of the body portion in the second channel 78. The flanges 86 are formed such that the distance between them forms a friction fit which retains at least a portion of the elongated tubular body 15. One feature of the flanges 86 is that they are intended to retain the elongated tubular body 15, and require a more substantial force to insert the tubular body 15 into or remove the body 15 by being frictionally pulled past flanges 86.

A third channel 88 is formed in the instrument holding member 12 and receives the working distal end 17 of the instrument therein. The third channel 88 further acts as a foot for balancing either when standing individually or stacked.

Figure 8:
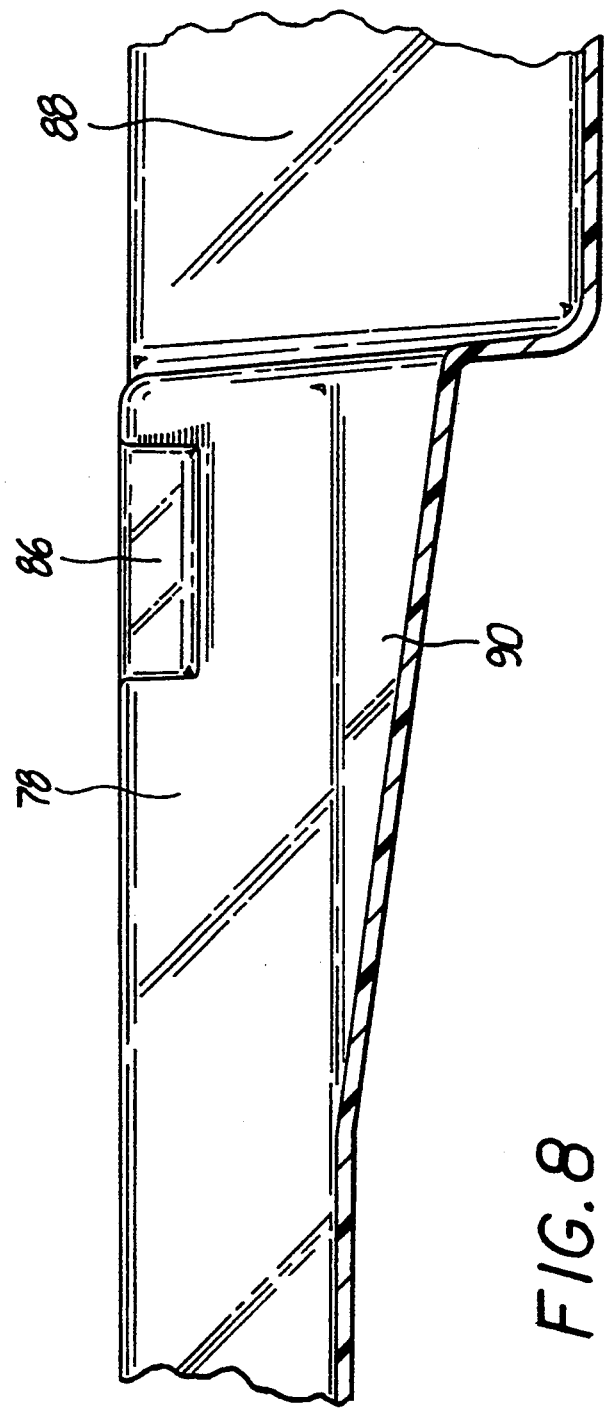
FIG. 8 is a cross-sectional view of the instrument holding member of the package taken along line 8—8 of FIG. 5.

Referring to FIGS. 7 and 8, a downwardly extending portion 90 is formed in the distal end of the second channel 78 below the pair of body flanges 86. The downwardly extending channel 90 provides a channel for movement of the distal working end 17 of the instrument to remove the working distal end 17 from its engagement by the pair of body flanges 86. The downwardly extending channel 90 extends distally and downwardly from the second channel 78 to the third channel 88, such that the depth of the downwardly extending channel 90 is greater than the depth of the second channel 78.

In use, the elongated surgical instrument 11' is loaded into the rigid instrument holding member 12' by first inserting the instrument distal working end 17 into the second channel 78 and under the body flanges 86 such that the distal end of the instrument elongated portion 15 and the distal working end 17 are retained by the body flanges 86. The instrument handle portion 13' is then inserted into the first portion 60 and under the first pair of flanges 76.

The surgical instrument 11 is released from the instrument holding member 12' by first grasping the handle portion 13' in the area of the grasping portion 64. The above steps are then reversed and the handle portion 13' is removed from its engagement by the first pair of flanges 76. The handle portion 13' is then pulled proximally such that the instrument distal working end 17 is moved along the downwardly extending portion 90 of the second channel 76 and out of engagement by the second pair of flanges 86.

Figure 9:
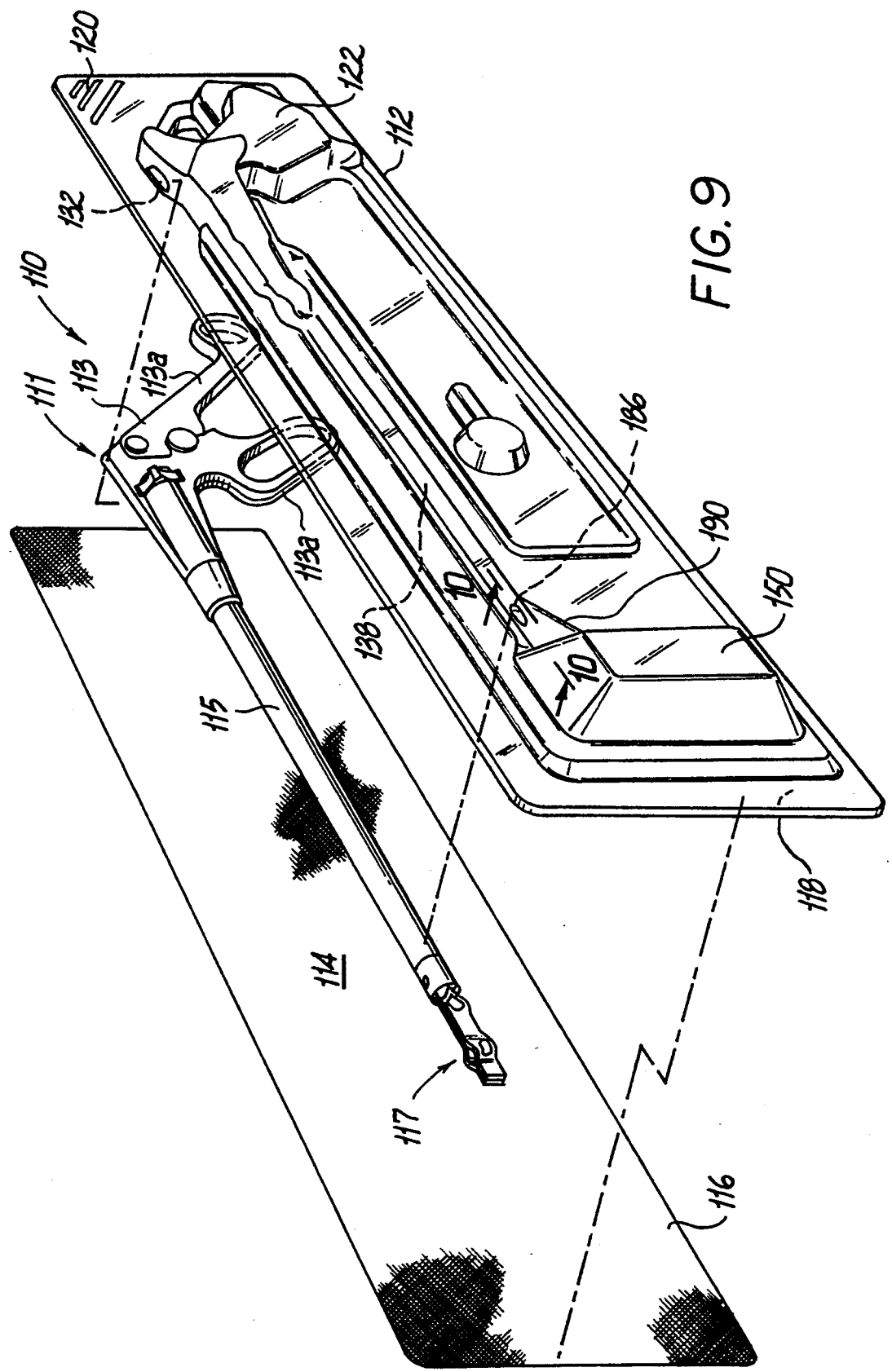
FIG. 9 is an exploded perspective view of a package in accordance with an alternative embodiment of the present invention.

Yet another embodiment of the invention is shown in FIG. 9 and including an instrument holder having many similar features of the earlier described embodiments. In this embodiment, the handle retaining flange 132 retains the handle 113 in the handle channel 122 and acts, as with the first embodiment, as a camming surface about which the handle 113 is pivoted for removal by the user. This embodiment also includes a downwardly extending portion 190 which extends distally and downwardly from the second channel to 178 to the third channel 188, with the depth of the downwardly extending channel 190 being greater than the depth of the second channel 178.

In use, the elongated surgical instrument 11 is loaded into the rigid instrument holding member 12 by first inserting the instrument distal working end 117 into the second channel 138, along downwardly extending portion 190 and under a second pair of flanges 186 such that the distal end of the instrument elongated portion 115 and the distal working end 117 are retained by the second pair of flanges 186. The instrument handle portion 113 is then inserted into the first channel, with the upper portion of the handle 113 being under the handle retaining flange 132 to be engaged therewith.

The surgical instrument is released form the instrument holding member 112 by first grasping the finger ring portions 113a of the handle and rotating the finger ring portions 113a away from the instrument holding member 112 and towards open top 130. As with the first embodiment, the handle retaining flange 132, the handle portion 113 is cammed about and removed from its engagement with handle retaining flange 132. The handle portion 113 is then pulled proximally such that the working end 117 of the instrument passes along the downwardly extending portion 190 and out from its engagement by the second pair of flanges 186.

Having now described the invention in specific detail and exemplified the manner in which it may be carried into practice, it will be readily apparent to those skilled in the art that innumerable variations, applications, modifications and extensions of the basic principles involved may be made without departing from its spirit or scope. By way of example only, the depth, width and relative position of the channels may vary widely based on personal preference and the particular surgical instrument to be packaged.

What is claimed is:

1. A package for an elongated instrument having a proximal portion, an elongated body portion and a distal end, the package comprising:
   a rigid instrument holding member having a base;
   a proximal channel in the base of the instrument holding member for receiving the instrument proximal portion, said proximal channel having a pair of side walls, a bottom wall and an open top;
   a first pair of opposing flanges extending across a portion of said proximal channel open top and from said proximal channel side wall for retaining the instrument proximal portion in said proximal channel;
   a body receiving channel in the base of the instrument holding member for receiving the instrument body portion, said body receiving channel defined by a pair of side walls, a bottom wall and an open top;
   a distal end receiving channel in the base of the instrument holding member for receiving the instrument distal end; and
   a second pair of opposing flanges extending from said body channel side walls across a portion of said body channel open top for retaining the instrument body portion in said body receiving channel wherein a first distance separates said first pair of flanges and a second distance separates said second pair of flanges, such that the distance between the said first pair of flanges is greater than the distance between said second pair of flanges.

2. A package as in claim 1 further comprising a cover member adapted to be mounted to and enclose the instrument holding member.

3. A package as in claim 1 wherein said instrument holding member is fabricated from a transparent plastic.

4. A package for an endoscopic instrument having a handle portion, an elongated body portion and a working end, the package comprising:
   a rigid instrument holding member having a base;
   a handle channel in the base of the instrument holding member for receiving the instrument handle portion, said handle channel defined by a pair of side walls, a bottom wall and an open top;
   at least one flange extending across said handle channel open top for retaining the instrument handle in said handle channel;
   a body portion receiving channel in the base of the instrument holding member for receiving the instrument body portion, said body receiving channel defined by a pair of side walls, a bottom wall and an open top;
   a working end receiving channel in the base of the instrument holding member for receiving the instrument working end;
   a pair of flanges extending across said body receiving channel open top for retaining the instrument body portion in said body receiving channel; and
   a downwardly extending portion formed in said body receiving channel, wherein said downwardly extending portion extends distally and downwardly to said working end receiving channel and wherein said working end receiving channel has a depth greater than said body receiving channel.

5. A package as in claim 4 where said downwardly extending portion is integral with said working end receiving channel such that the instrument working end may be moved along said body receiving channel bottom out from engagement with said pair of flanges extending across said body receiving channel.

6. A package as in claim 5 wherein said pair of flanges are positioned in a first plane substantially above said downwardly extending portion.

7. A package for an elongated surgical instrument having a handle portion, an elongated body portion and a working end, the package comprising:
   a rigid instrument holding member having a base;
   a handle receiving channel in the base of the instrument holding member for receiving the instrument handle portion;
   a body receiving channel in the base of the instrument holding member for receiving the instrument elongated body;
   a working end receiving channel in the base of the instrument holding member for receiving the instrument working end;
   a handle retaining flange extending across a portion of said handle receiving channel to retain a portion of the instrument handle in said handle receiving channel; at least one body retaining flange extending across a portion of said body receiving channel for retaining the instrument body portion in said body receiving channel; and
   a downwardly extending portion formed in said elongated receiving channel, wherein said downwardly extending portion extends distally and downwardly to said working end receiving channel and wherein said working end receiving channel has a depth greater than said body receiving channel.

8. A package as in claim 7 wherein said handle receiving channel is defined by at least one side wall, a bottom wall and an open top, said handle retaining flange extending from said at least one side wall.

9. A package as in claim 7 further comprising a cover member adapted to be mounted to and enclose the instrument holding member.

10. A package as in claim 9 wherein said cover member is adhesively bonded to the instrument holding member such that the cover member can be peeled away from the instrument holding member.

11. A package as in claim 7 wherein said instrument holding member is fabricated from a transparent plastic.

12. A package as in claim 7 wherein said handle retaining flange is integral with said at least one handle receiving channel side wall.

* * * * *